(12) United States Patent
Kim et al.

(10) Patent No.: US 11,759,145 B1
(45) Date of Patent: Sep. 19, 2023

(54) TECHNIQUE FOR IDENTIFYING DEMENTIA BASED ON VOICE DATA

(71) Applicant: HAII corp., Seoul (KR)

(72) Inventors: Ho Yung Kim, Seoul (KR); Dong Han Kim, Seoul (KR); Hye Bin Hwang, Incheon (KR); Chan Yeong Park, Seoul (KR); Ji An Choi, Seoul (KR); Hyun Jeong Ko, Seoul (KR); Su Yeon Park, Seoul (KR); Byung Hun Yun, Seoul (KR)

(73) Assignee: HAII CORP., Seoul (KR)

( * ) Notice: Subject to any disclaimer, the term of this patent is extended or adjusted under 35 U.S.C. 154(b) by 0 days.

(21) Appl. No.: 18/316,124

(22) Filed: May 11, 2023

(30) Foreign Application Priority Data

Jun. 9, 2022 (KR) .................. 10-2022-0069864

(51) Int. Cl.
*A61B 5/00* (2006.01)
*G16H 50/20* (2018.01)

(52) U.S. Cl.
CPC .......... *A61B 5/4803* (2013.01); *A61B 5/4088* (2013.01); *G16H 50/20* (2018.01)

(58) Field of Classification Search
CPC ............................. A61B 5/4803; A61B 5/4088
See application file for complete search history.

(56) References Cited

FOREIGN PATENT DOCUMENTS

| JP | 2021097913 A | 7/2021 |
|---|---|---|
| KR | 1020190135908 A | 12/2019 |
| KR | 102257291 B1 | 5/2021 |
| KR | 1020210091561 A | 7/2021 |
| KR | 102314213 B1 | 10/2021 |
| KR | 102321197 B1 | 11/2021 |
| KR | 1020210155335 A | 12/2021 |
| KR | 1020220031957 A | 3/2022 |
| KR | 102392318 B1 | 5/2022 |
| KR | 102321197 | 7/2022 |

OTHER PUBLICATIONS

Korea Patent Office, Office Action, dated Nov. 16, 2022.

*Primary Examiner* — Scott M. Getzow
(74) *Attorney, Agent, or Firm* — Umberg Zipser LLP

(57) ABSTRACT

Disclosed is a method of identifying dementia by at least one processor of a device. The method may include obtaining content analysis information and voice activity analysis information by using a plurality of first voice data and second voice data which have been obtained by performing a plurality of tasks in a user terminal, and identifying dementia by inputting the content analysis information and the voice activity analysis information to a dementia identification model.

12 Claims, 9 Drawing Sheets

Fig. 5

| Story title | Number of images |
|---|---|
| Rabbit and Turtle | 4 |
| Kongjwi Patjwi | 4 |
| Sun and Moon | 4 |
| Heungbu and Nolbu | 5 |

| Keyword | Analogue | | | | | | | |
|---|---|---|---|---|---|---|---|---|
| Tease | vex | romp | enrage | mock | pasquinade | make sarcastic | ridicule | taunt | flirt | Feel twinge |
| | hurt feeling | carp | Small-minded | Smile cynically | Be sarcastic | | | | |
| Run | competition | race | bet | game | contest | | | | |
| Slow | Slow | Late | Go slowly | belated | Rather late | Somewhat late | | | |
| Fast | Be fast | urgent | swift | rapid | urgency | nimble | quick | agile | |
| Do | suggest | present | request | ask | seek | Offer condition | | | prompt |

Fig. 9

TECHNIQUE FOR IDENTIFYING DEMENTIA BASED ON VOICE DATA

BACKGROUND

1. Technical Field

The present disclosure relates to a technique for identifying dementia based on voice data and, more particularly, to an apparatus and method for identifying dementia by using a plurality of first voice data that is obtained while a plurality of images is displayed and a second voice data that is obtained without displaying an image.

2. Related Art

Alzheimer's disease (AD), which is a brain disease caused by aging, causes progressive memory impairment, cognitive deficits, changes in individual personality, etc. In addition, dementia refers to a state of persistent and overall cognitive function decline that occurs when a person who has led a normal life suffers from damage to brain function due to various causes. In this case, a cognitive function refers to various intellectual abilities, such as memory, the language ability, the temporal and spatial understanding ability, the judgment ability, and the abstract thinking ability. Each cognitive function is closely related to a specific part of the brain. The most common form of dementia is Alzheimer's disease.

Various methods have been proposed for diagnosing Alzheimer's disease, dementia, or mild cognitive impairment. For example, a method of diagnosing Alzheimer's disease or mild cognitive impairment using the expression level of miR-206 in the olfactory tissue, and a method for diagnosing dementia using a biomarker that characteristically increases in blood are known.

However, since special equipment or tests necessary for biopsy are required so as to use miR-206 in the olfactory tissue, and blood from a patient should be collected by an invasive method so as to use biomarkers in blood, there is a disadvantage that the patient's rejection feeling is relatively large.

Therefore, there is an urgent need for development of a dementia diagnosis method where patients hardly feel rejection without a separate special equipment or examination.

SUMMARY

The present disclosure has been made in view of the above problems, and it is one object of the present disclosure to provide an accurate dementia diagnosis method where patients hardly feel rejection.

It will be understood that technical problems of the present disclosure are not limited to the aforementioned problem and other technical problems not referred to herein will be clearly understood by those skilled in the art from the description below.

In an embodiment, a method of identifying dementia, which is performed by at least one processor of a device may include obtaining content analysis information and voice activity analysis information by using a plurality of first voice data and a second voice data which have been obtained by performing a plurality of tasks in a user terminal, and identifying dementia by inputting the content analysis information and the voice activity analysis information to a dementia identification model.

According to some embodiments of the present disclosure, the obtaining of the content analysis information and the voice activity analysis information by using the plurality of first voice data and the second voice data which have been obtained by performing the plurality of tasks in the user terminal may include changing the plurality of first voice data into a plurality of first text data, converting the second voice data into second text data, and obtaining the content analysis information by using the plurality of first text data and the second text data.

According to some embodiments of the present disclosure, the content analysis information may include first information on a ratio of an interjection to all syllables of the plurality of first text data and the second text data.

According to some embodiments of the present disclosure, the content analysis information may further include second information indicative of a degree in which a keyword related to each of the plurality of images is included in each of the plurality of first text data and the second text data and third information indicative of a degree in which an analogue of the keyword related to each of the plurality of images is included in each of the plurality of first text data and the second text data.

According to some embodiments of the present disclosure, the voice activity analysis information may include speech rate information of a user of the user terminal and response time information of the user.

According to some embodiments of the present disclosure, the response time information may include information calculated based on information on first timing at which a voice of the user is present in each of the plurality of first voice data, and information calculated based on information on second timing at which a voice of the user is present in the second voice data.

According to some embodiments of the present disclosure, the plurality of tasks may include a first task for obtaining the plurality of first voice data related to the plurality of images, respectively, while operating in conjunction with the sequential displaying of the plurality of images, and a second task for obtaining the second voice data without displaying an image.

According to some embodiments of the present disclosure, the plurality of first voice data may be voice data that is obtained from timing at which a first touch input is input to timing at which a second touch input is input when an N-th image, among the plurality of images, is displayed. The N may be a natural number equal to or greater than 1.

According to some embodiments of the present disclosure, the first touch input may be a touch input to a first button that is displayed in the user terminal along with the N-th image. The second touch input may be a touch input to a second button in the state in which the second button has been displayed in the user terminal along with the N-th image, instead of the first button, in response to the first touch input.

According to some embodiments of the present disclosure, the N-th image may be changed into an (N+1)-th image in response to the second touch input.

According to some embodiments of the present disclosure, the second voice data may be voice data that is obtained from timing at which a third touch input is input to timing at which a fourth touch input is input on a screen that is displayed when the second task is performed.

According to some embodiments of the present disclosure, the third touch input may be a touch input to a third button that is displayed when the second task is performed, and the fourth touch input may be a touch input to a fourth button in a state in which the fourth button has been displayed instead of the third button, in response to the third touch input.

In an embodiment, a computer program stored in a computer-readable storage medium may perform steps of identifying dementia when the computer program is executed by at least one processor of a device. The steps may include obtaining content analysis information and voice activity analysis information by using a plurality of first voice data and second voice data which have been obtained by performing a plurality of tasks, and identifying dementia by inputting the content analysis information and the voice activity analysis information to a dementia identification model.

In an embodiment, an apparatus for identifying dementia storage in which at least one program instruction has been stored, and at least one processor configured to perform the at least one program instruction. The at least one processor may obtain content analysis information and voice activity analysis information by using a plurality of first voice data and second voice data which have been obtained by performing a plurality of tasks, and may identify dementia by inputting the content analysis information and the voice activity analysis information to a dementia identification model.

The technical solutions obtainable in the present disclosure are not limited to the above-mentioned solutions, other solutions not mentioned will be clearly understood by those skilled in the art from the description below.

Effects of the technique for identifying dementia using voice data according to the present disclosure will be described as follows.

According to some embodiments of the present disclosure, an accurate dementia diagnosis method where patients hardly feel rejection is provided.

It will be understood that effects obtained by the present disclosure are not limited to the aforementioned effect and other effects not referred to herein will be clearly understood by those skilled in the art from the description below.

BRIEF DESCRIPTION OF THE DRAWINGS

Various embodiments of the present disclosure are described with reference to the accompanying drawings. In this case, like reference numbers are used to refer to like elements. In the following embodiments, numerous specific details are set forth so as to provide a thorough understanding of one or more embodiments for purposes of explanation. It will be apparent, however, that such embodiment(s) may be practiced without these specific details.

FIGS. 4 and 5 are diagrams for describing a plurality of images that is displayed when a plurality of first voice data is obtained according to some embodiments of the present disclosure.

FIG. 9 is a diagram for describing an example of keywords and analogues which are used when content analysis information is obtained according to some embodiments of the present disclosure.

DETAILED DESCRIPTION

Figure 1:
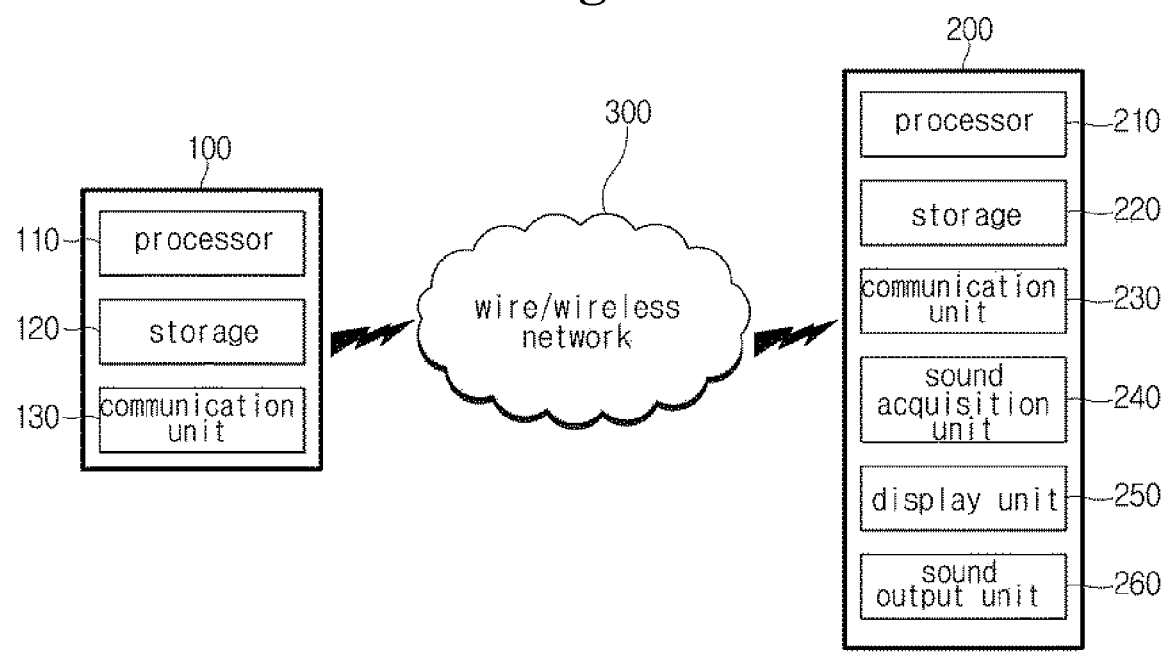
FIG. 1 is a schematic diagram for explaining a system for identifying dementia according to some embodiments of the present disclosure.

Hereinafter, various embodiments of an apparatus according to the present disclosure and a method of controlling the same will be described in detail with reference to the accompanying drawings. Regardless of the reference numerals, the same or similar components are assigned the same reference numerals, and overlapping descriptions thereof will be omitted.

Objectives and effects of the present disclosure, and technical configurations for achieving the objectives and the effects will become apparent with reference to embodiments described below in detail in conjunction with the accompanying drawings. In describing one or more embodiments of the present disclosure, a detailed description of known functions and configurations incorporated herein will be omitted when it may make the subject matter of the present disclosure unclear.

The terms used in the specification are defined in consideration of functions used in the present disclosure, and can be changed according to the intent or conventionally used methods of clients, operators, and users. The features of the present disclosure will be more clearly understood from the accompanying drawings and should not be limited by the accompanying drawings, and it is to be appreciated that all changes, equivalents, and substitutes that do not depart from the spirit and technical scope of the present disclosure are encompassed in the present disclosure.

The suffixes "module" and "unit" of elements herein are used for convenience of description and thus can be used interchangeably and do not have any distinguishable meanings or functions.

Terms including an ordinal number, such as first, second, etc., may be used to describe various elements, but the elements are not limited by the terms. The above terms are used only for the purpose of distinguishing one component from another component. Therefore, a first component mentioned below may be a second component within the spirit of the present description.

A singular expression includes a plural expression unless the context clearly dictates otherwise. That is, a singular expression in the present disclosure and in the claims should generally be construed to mean "one or more" unless specified otherwise or if it is not clear from the context to refer to a singular form.

The terms such as "include" or "comprise" may be construed to denote a certain characteristic, number, step, operation, constituent element, or a combination thereof, but may not be construed to exclude the existence of or a possibility of addition of one or more other characteristics, numbers, steps, operations, constituent elements, or combinations thereof.

The term "or" in the present disclosure should be understood as "or" in an implicit sense and not "or" in an exclusive sense. That is, unless otherwise specified or clear from context, "X employs A or B" is intended to mean one of natural implicit substitutions. That is, when X employs A; when X employs B; or when X employs both A and B, "X employs A or B" can be applied to any one of these cases. Furthermore, the term "and/or" as used in the present disclosure should be understood to refer to and encompass all possible combinations of one or more of listed related items.

As used in the present disclosure, the terms "information" and "data" may be used interchangeably.

Unless otherwise defined, all terms (including technical and scientific terms) used in the present disclosure may be used with meanings that can be commonly understood by those of ordinary skill in the technical field of the present disclosure. Also, terms defined in general used dictionary are not to be excessively interpreted unless specifically defined.

However, the present disclosure is not limited to embodiments disclosed below and may be implemented in various different forms. Some embodiments of the present disclosure are provided merely to fully inform those of ordinary skill in the technical field of the present disclosure of the scope of the present disclosure, and the present disclosure is only defined by the scope of the claims. Therefore, the definition should be made based on the content throughout the present disclosure.

According to some embodiments of the present disclosure, a processor of a user terminal may obtain voice data that is digital biomarker data for dementia identification. Here, the digital biomarker data is a biomarker acquired through a digital device such as a mobile phone, and may be a biomarker used for dementia identification in the present disclosure.

Hereinafter, a system for identifying dementia will be described with reference to FIG. 1, a method of obtaining voice data, which is digital biomarker data for dementia identification, will be described with reference to FIGS. 2 to 7, a method of identifying dementia using voice data, which is digital biomarker data, will be described with reference to FIGS. 8 and 9.

FIG. 1 is a schematic diagram for explaining a system for identifying dementia according to some embodiments of the present disclosure.

Referring to FIG. 1, the system for identifying dementia may include a device 100 for identifying dementia and a user terminal 200 for a user requiring dementia identification. Here, the user terminal 200 may be a terminal used by a user who needs dementia identification. However, it is not limited thereto.

The device 100 and the user terminal 200 may be connected to communication over a wire/wireless network 300. However, the components constituting the system illustrated in FIG. 1 are not essential in implementing the system for identifying dementia, and thus more or fewer components than those listed above may be included.

The device 100 of the present disclosure may be paired with or connected to the user terminal 200 over the wire/wireless network 300, thereby transmitting/receiving predetermined data. In this case, data transmitted/received over the wire/wireless network 300 may be converted before transmission/reception. In this case, the "wire/wireless network" 300 collectively refers to a communication network supporting various communication standards or protocols for pairing and/or data transmission/reception between the device 100 and the user terminal 200. The wire/wireless network 300 includes all communication networks to be supported now or in the future according to the standard and may support all of one or more communication protocols for the same.

The device 100 for identifying dementia may include a processor 110, storage 120, and a communication unit 130. The components illustrated in FIG. 1 are not essential for implementing the device 100, and thus, the device 100 described in the present disclosure may include more or fewer components than those listed above.

Each component of the device 100 of the present disclosure may be integrated, added, or omitted according to the specifications of the device 100 that is actually implemented. That is, as needed, two or more components may be combined into one component or one component may be subdivided into two or more components. In addition, a function performed in each block is for describing an embodiment of the present disclosure, and the specific operation or device does not limit the scope of the present disclosure.

The device 100 described in the present disclosure may include any device that transmits and receives at least one of data, content, service, and application, but the present disclosure is not limited thereto.

The device 100 of the present disclosure includes, for example, any standing devices such as a server, a personal computer (PC), a microprocessor, a mainframe computer, a digital processor and a device controller; and any mobile devices (or handheld device) such as a smart phone, a tablet PC, and a notebook, but the present disclosure is not limited thereto.

In an embodiment of the present disclosure, the term "server" refers to a device or system that supplies data to or receives data from various types of user terminals, i.e., a client.

For example, a web server or portal server that provides a web page or web content (or a web service), an advertising server that provides advertising data, a content server that provides content, an SNS server that provides a social network service (SNS), a service server provided by a manufacturer, a multichannel video programming distributor (MVPD) that provides video on demand (VoD) or a streaming service, a service server that provides a pay service, or the like may be included as a server.

In an embodiment of the present disclosure, the device 100 means a server according to context, but may mean a fixed device or a mobile device, or may be used in an all-inclusive sense unless specified otherwise.

The processor 110 may generally control the overall operation of the device 100 in addition to an operation related to an application program. The processor 110 may provide or process appropriate information or functions by processing signals, data, or information that is input or output through the components of the device 100 or driving an application program stored in the storage 120.

The processor 110 may control at least some of the components of the device 100 to drive an application program stored in the storage 120. Furthermore, the processor 110 may operate by combining at least two or more of the components included in the device 100 to drive the application program.

The processor 110 may include one or more cores, and may be any of a variety of commercial processors. For example, the processor 110 may include a central processing unit (CPU), general purpose graphics processing unit (GPGPU), and tensor processing unit (TPU) of the device, but the present disclosure is not limited thereto.

The processor 110 of the present disclosure may be configured as a dual processor or other multiprocessor architecture, but the present disclosure is not limited thereto.

The processor 110 may identify whether a user has dementia using the dementia identification model according to some embodiments of the present disclosure by reading a computer program stored in the storage 120.

The storage 120 may store data supporting various functions of the device 100. The storage 120 may store a plurality of application programs (or applications) driven in the device 100, and data, commands, and at least one program command for the operation of the device 100. At least some of these application programs may be downloaded from an external server through wireless communication. In addition, at least some of these application programs may exist in the device 100 from the time of shipment for basic functions of the device 100. The application program may be stored in the storage 120, installed in the device 100, and driven by the processor 110 to perform the operation (or function) of the device 100.

The storage 120 may store any type of information generated or determined by the processor 110 and any type of information received through the communication unit 130.

The storage 120 may include at least one type of storage medium of a flash memory type, a hard disk type, a solid state disk (SSD) type, a silicon disk drive (SDD) type, a multimedia card micro type, a card-type memory (e.g., SD memory and XD memory), random access memory (RAM), static random access memory (SRAM), read-only memory (ROM), electrically erasable programmable read-only memory (EEPROM), programmable read-only memory (PROM), magnetic memory, a magnetic disk, and an optical disk. The device 100 may be operated in relation to a web storage that performs a storage function of the storage 120 on the Internet.

According to some embodiments of the present disclosure, a pre-learned dementia identification model may be stored in the storage 120 of the device 100.

The dementia identification model may be trained by a method of updating the weight of a neural network by back-propagating a difference value between label data labeled in input data for learning and prediction data output from the dementia identification model.

In the present disclosure, input data for learning may be acquired by each of a plurality of test users performing a plurality of tasks according to some embodiments of the present disclosure through their own test device. Here, the input data for learning may be content analysis information for learning and voice activity analysis information for learning obtained by using a plurality of first voice data for learning and second voice data for learning obtained by performing a plurality of tasks. However, it is not limited thereto.

In an embodiment of the present disclosure, the test users may include a user classified as a patient with mild cognitive impairment (MCI), a user classified as an Alzheimer's patient, a user classified as normal, but the present disclosure is not limited thereto.

In an embodiment of the present disclosure, the test device may refer to a device where various test users perform tests when securing input data for learning. In this case, the test device may be a mobile device, such as a mobile phone, a smart phone, a tablet PC, or an ultrabook, similarly to the user terminal 200 used for dementia identification, but the present disclosure is not limited thereto.

In an embodiment of the present disclosure, the label data may be a score value capable of recognizing whether a patient is normal, is an Alzheimer's patient, and a patient with mild cognitive impairment, but the present disclosure is not limited thereto.

A dementia identification model may be composed of a set of interconnected computational units, which may generally be referred to as nodes. These nodes may also be referred to as neurons. The neural network may be configured to include at least one node. Nodes (or neurons) constituting the neural network may be interconnected by one or more links.

In the dementia identification model, one or more nodes connected through a link may relatively form a relationship between an input node and an output node. The concepts of an input node and an output node are relative, and any node in an output node relationship with respect to one node may be in an input node relationship in a relationship with another node, and vice versa. As described above, an input node-to-output node relationship may be created around a link. One output node may be connected to one input node through a link, and vice versa.

In the relation between the input node and the output node connected through one link, a value of data of the output node may be determined based on data that is input to the input node. In this case, the link interconnecting the input node and the output node may have a weight. The weight may be variable, and may be changed by a user or an algorithm so that the neural network performs a desired function.

For example, when one or more input nodes are connected to one output node by each link, the output node may determine an output node value based on values that are input to input nodes connected to the output node and based on a weight set in a link corresponding to each input node.

As described above, in the dementia identification model, one or more nodes may be interconnected through one or more links to form an input node and output node relationship in the neural network. The characteristics of the dementia identification model may be determined according to the number of nodes and links in the dementia identification model, a correlation between nodes and links, and a weight value assigned to each of the links.

The dementia identification model may consist of a set of one or more nodes. A subset of nodes constituting the dementia identification model may constitute a layer. Some of the nodes constituting the dementia identification model may configure one layer based on distances from an initial input node. For example, a set of nodes having a distance of n from the initial input node may constitute n layers. The distance from the initial input node may be defined by the minimum number of links that should be traversed to reach the corresponding node from the initial input node. However, the definition of such a layer is arbitrary for the purpose of explanation, and the order of the layer in the dementia identification model may be defined in a different way from that described above. For example, a layer of nodes may be defined by a distance from a final output node.

The initial input node may refer to one or more nodes to which the input data for learning is directly input without going through a link in a relationship with other nodes among nodes in the neural network. Alternatively, in a relationship between nodes based on a link in the dementia identification model, it may mean nodes that do not have other input nodes connected by a link. Similarly, the final output node may refer to one or more nodes that do not have an output node in relation to other nodes among nodes in the neural network. In addition, a hidden node may refer to nodes constituting the neural network other than the first input node and the last output node.

In the dementia identification model according to some embodiments of the present disclosure, the number of nodes in the input layer may be greater than the number of nodes in the output layer, and the neural network may have a form in which the number of nodes decreases as it progresses from the input layer to the hidden layer. In addition, input data for learning may be input to each node of the input layer. However, it is not limited thereto.

According to some embodiments of the present disclosure, the dementia identification model may have a deep neural network structure.

A deep neural network (DNN) may refer to a neural network including a plurality of hidden layers in addition to an input layer and an output layer. The DNN may be used to identify the latent structures of data.

The DNN may include convolutional neural networks (CNNs), recurrent neural networks (RNNs), auto encoders, generative adversarial networks (GANs), and restricted Boltzmann machines (RBM), a deep belief network (DBN), a Q network, a U network, a Siamese network, and a generative adversarial network (GAN). These DNNs are only provided as examples, and the present disclosure is not limited thereto.

The dementia identification model of the present disclosure may be learned in a supervised learning manner, but the present disclosure is not limited thereto. The dementia identification model may be learned in at least one manner of unsupervised learning, semi supervised learning, or reinforcement learning.

The learning of the dementia identification model may be a process of applying knowledge for performing an operation of identifying dementia by the dementia identification model to a neural network.

The dementia identification model can be trained in a way to minimize output errors. Learning of the dementia identification model is a process of repeatedly inputting the input data for learning into the dementia identification model, calculating errors of an output (score value predicted through the neural network) and target (score value used as label data) of the dementia identification model on the input data for learning, and updating the weight of each node of the dementia identification model by back-propagating the error of the dementia identification model from an output layer of the dementia identification model to an input layer in a direction of reducing the error.

A change amount of a connection weight of each node to be updated may be determined according to a learning rate. Calculation of the dementia identification model on the input data and back-propagation of errors may constitute a learning cycle (epoch). The learning rate may be differently applied depending on the number of repetitions of a learning cycle of the dementia identification model. For example, in an early stage of learning the dementia identification model, a high learning rate may be used to enable the dementia identification model to quickly obtain a certain level of performance, thereby increasing efficiency, and, in a late stage of learning the dementia identification model, accuracy may be increased by using a low learning rate.

In the learning of the dementia identification model, the input data for learning may be a subset of actual data (i.e., data to be processed using the learned dementia identification model), and thus, there may be a learning cycle wherein errors for the input data for learning decrease but errors for real data increase. Overfitting is a phenomenon wherein errors on actual data increase due to over-learning on input data for learning as described above.

Overfitting may act as a cause of increasing errors in a machine learning algorithm. To prevent such overfitting, methods, such as increasing the input data for learning, regularization, and dropout that deactivate some of nodes in a network during a learning process, and the utilization of a batch normalization layer, may be applied.

According to some embodiments of the present disclosure, the storage 120 may store a plurality of images for a plurality of stories, respectively. In this case, the plurality of images may be images that are sequentially displayed when a plurality of first voice data is obtained. Furthermore, a plurality of different images may be stored in the plurality of stories. This is more specifically described with reference to FIGS. 4 and 5.

The communication unit 130 may include one or more modules that enable wire/wireless communication between the device 100 and a wire/wireless communication system, between the device 100 and another device, or between the device 100 and an external server. In addition, the communication unit 130 may include one or more modules that connect the device 100 to one or more networks.

The communication unit 130 refers to a module for wired/wireless Internet connection, and may be built-in or external to the device 100. The communication unit 130 may be configured to transmit and receive wire/wireless signals.

The communication unit 130 may transmit/receive a radio signal with at least one of a base station, an external terminal, and a server on a mobile communication network constructed according to technical standards or communication methods for mobile communication (e.g., Global System for Mobile communication (GSM), Code Division Multi Access (CDMA), Code Division Multi Access 2000 (CDMA2000), Enhanced Voice-Data Optimized or Enhanced Voice-Data Only (EV-DO), Wideband CDMA (WCDMA), High Speed Downlink Packet Access (HSDPA), High Speed Uplink Packet Access (HSUPA), Long Term Evolution (LTE), Long Term Evolution-Advanced (LTE-A), etc.).

Examples of wireless Internet technology include Wireless LAN (WLAN), Wireless-Fidelity (Wi-Fi), Wireless Fidelity (Wi-Fi) Direct, Digital Living Network Alliance (DLNA), Wireless Broadband (WiBro), World Interoperability for Microwave Access (WiMAX), High Speed Downlink Packet Access (HSDPA), High Speed Uplink Packet Access (HSUPA), Long Term Evolution (LTE), and Long Term Evolution-Advanced (LTE-A). However, in a range including Internet technologies not listed above, the communication unit 130 may transmit/receive data according to at least one wireless Internet technology.

In addition, the communication unit 130 may be configured to transmit and receive signals through short range communication. The communication unit 130 may perform short range communication using at least one of Bluetooth™, Radio Frequency Identification (RFID), Infrared Data Association (IrDA), Ultra-Wideband (UWB), ZigBee, Near Field Communication (NFC), Wireless-Fidelity (Wi-Fi), Wi-Fi Direct and Wireless Universal Serial Bus (Wireless USB) technology. The communication unit 130 may support wireless communication through short range communication networks (wireless area networks). The short range communication networks may be wireless personal area networks.

The device 100 according to some embodiments of the present disclosure may be connected to the user terminal 200 and the wire/wireless network 300 through the communication unit 130.

In an embodiment of the present disclosure, the user terminal 200 may be paired with or connected to the device 100, in which the dementia identification model is stored, over the wire/wireless network 300, thereby transmitting/receiving and displaying predetermined data.

The user terminal 200 described in the present disclosure may include any device that transmits, receives, and displays at least one of data, content, service, and application. In addition, the user terminal 200 may be a terminal of a user who wants to check dementia, but the present disclosure is not limited thereto.

In an embodiment of the present disclosure, the user terminal 200 may include, for example, a mobile device such as a mobile phone, a smart phone, a tablet PC, or an ultrabook, but the present disclosure is not limited thereto. The user terminal 200 may include a standing device such as a Personal Computer (PC), a microprocessor, a mainframe computer, a digital processor, or a device controller.

The user terminal 200 includes a processor 210, storage 220, a communication unit 230, a sound acquisition unit 240, a display unit 250 and a sound output unit 260. The components illustrated in FIG. 1 are not essential in implementing the user terminal 200, and thus, the user terminal 200 described in the present disclosure may have more or fewer components than those listed above.

Each of the components of the user terminal 200 of the present disclosure may be integrated, added, or omitted according to the specifications of the user terminal 200 that is actually implemented. That is, as needed, two or more components may be combined into one component, or one component may be subdivided into two or more components. In addition, the function performed in each block is for describing an embodiment of the present disclosure, and the specific operation or device does not limit the scope of the present disclosure.

The processor 210, storage 220, and communication unit 230 of the user terminal 200 are the same components as the processor 110, storage 120, and communication unit 130 of the device 100, and thus redundant descriptions thereof will be omitted, and differences between them are chiefly described below.

In the present disclosure, the processor 210 of the user terminal 200 may control the display unit 250 so that the display unit displays a screen for obtaining voice data. In this case, the screen for obtaining voice data may be a screen on which each of a plurality of images related to a story is displayed, but the present disclosure is not limited thereto.

According to some embodiments of the present disclosure, a plurality of images related to a story may be stored in the storage 120 of the device 100, and may also be stored in the storage 220 of the user terminal 200.

If a plurality of images has been stored in the storage 120 of the device 100, the processor 210 of the user terminal 200 may control the communication unit 230 so that the communication unit 230 receives a primary image (i.e., the first image), among the plurality of images, after transmitting a primary image request signal to the device 100 when the primary image is displayed. When the primary image is received, the processor 210 of the user terminal 200 may control the display unit 250 so that the display unit 250 displays the primary image. Next images may be displayed in the user terminal 200 by using the same method as the method of displaying the primary image, but the present disclosure is not limited thereto.

If a plurality of images has been stored in the storage 220 of the user terminal 200, the processor 210 of the user terminal 200 may control the display unit 250 so that the display unit 250 sequentially displays the plurality of images that has been stored in the storage 220.

Since high processing speed and computational power are required to perform an operation using the dementia identification model, the dementia identification model may be stored only in the storage 120 of the device 100 and may not be stored in the storage 220 of the user terminal 200, but the present disclosure is not limited thereto.

The sound acquisition unit 240 may process an external sound signal as electrical sound data. The processed sound data may be used in various ways according to a function (or a running application program) being performed by the user terminal 200. Various noise removal algorithms for removing noise generated in a process of receiving an external sound signal may be implemented in the sound acquisition unit 240.

In the present disclosure, the sound acquisition unit 240 may obtain recorded voice data of a voice of a user under the control of the processor 210, but the present disclosure is not limited thereto.

Specifically, the processor 210 of the user terminal 200 may obtain a plurality of first voice data related to a plurality of images, respectively, while the plurality of images is sequentially displayed.

More specifically, the processor 210 of the user terminal 200 may control the display unit 250 so that the display unit 250 also displays a first button (e.g., a start button) when displaying a primary image, among a plurality of images. When receiving a first touch input to the first button, the processor 210 may start to obtain voice data related to the primary image by activating the sound acquisition unit 240, while operating in conjunction with the displaying of a second button (e.g., a complete button) instead of the first button along with the primary image. Furthermore, when a second touch input to the second button is input, the processor 210 may terminate the acquisition of the voice data. That is, the voice data that is obtained when the primary image is displayed may be recorded voice data of a voice of a user from timing at which the first touch input is input to timing at which the second touch input is input.

The processor 210 of the user terminal 200 may obtain a plurality of first voice data related to a plurality of images, respectively, while displaying the plurality of images related to one story.

According to some embodiments of the present disclosure, the processor 210 may control the communication unit 230 so that the communication unit 230 transmits the plurality of first voice data to the device 100.

For example, the processor 210 may control the communication unit 230 so that the communication unit 230 transmits each of a plurality of first voice data to the device 100 in real time whenever the processor 210 obtains the plurality of first voice data.

As another example, when obtaining all of the plurality of first voice data, the processor 210 may control the communication unit 230 so that the communication unit 230 transmits the plurality of first voice data to the device 100.

As still another example, when obtaining all of second voice data without the display of an image after obtaining the plurality of first voice data, the processor 210 may control the communication unit 230 so that the communication unit 230 transmits the plurality of first voice data and the second voice data to the device 100.

However, the aforementioned examples are merely examples, and the present disclosure is not limited to the examples.

When obtaining a plurality of first voice data related to a plurality of images related to one story, respectively, the processor 210 of the user terminal 200 may control the sound acquisition unit 240 so that the sound acquisition unit 240 obtains second voice data without the display of an image.

Specifically, the processor 210 of the user terminal 200 may control the display unit 250 so that the display unit 250 also displays a message including contents indicating that all of the contents of a story need to be spoken along with a third button (e.g., the start button). When receiving a third touch input to the third button, the processor 210 may start to obtain second voice data related to a story by activating the sound acquisition unit 240, while operating in conjunction with the displaying of a fourth button (e.g., the complete button) instead of the third button along with the message. Furthermore, when a fourth touch input to the fourth button is input, the processor 210 may terminate the acquisition of the second voice data. That is, the second voice data may be recorded voice data of a voice of a user from timing at which the third touch input is input to a timing at which the fourth touch input is input.

The display unit 250 may display (output) information processed by the user terminal 200. For example, the display unit 250 may display execution screen information of an application program that is driven in the user terminal 200, or user interface (UI) and graphic user interface (GUI) information according to the execution screen information.

The display unit 250 may include at least one of a liquid crystal display (LCD), a thin film transistor liquid crystal display (TFT LCD), an organic light-emitting diode (OLED), a flexible display, a 3D display, and an e-ink display, but the present disclosure is not limited thereto.

The display unit 250 of the present disclosure may sequentially display a plurality of images related to a story, under the control of the processor 210.

The sound output unit 260 may output audio data (or sound data, etc.) received from the communication unit 230 or stored in the storage 220. The sound output unit 260 may also output a sound signal related to a function that is performed by the user terminal 200.

The sound output unit 260 may include a receiver, a speaker, or a buzzer. That is, the sound output unit 260 may be implemented as a receiver or may be implemented in the form of a loudspeaker, but the present disclosure is not limited thereto.

According to some embodiments of the present disclosure, the sound output unit 260 may output a preset sound (e.g., a voice that describes a task that needs to be performed by a user), while operating in conjunction with the output of a screen including a message that describes a task that needs to be performed by a user, before a plurality of images is displayed, but the present disclosure is not limited thereto.

According to some embodiments of the present disclosure, the processor 210 of the user terminal 200 may obtain a plurality of first voice data and second voice data, that is, digital bio marker data for identifying dementia. This is more specifically described with reference to FIG. 2.

Figure 2:
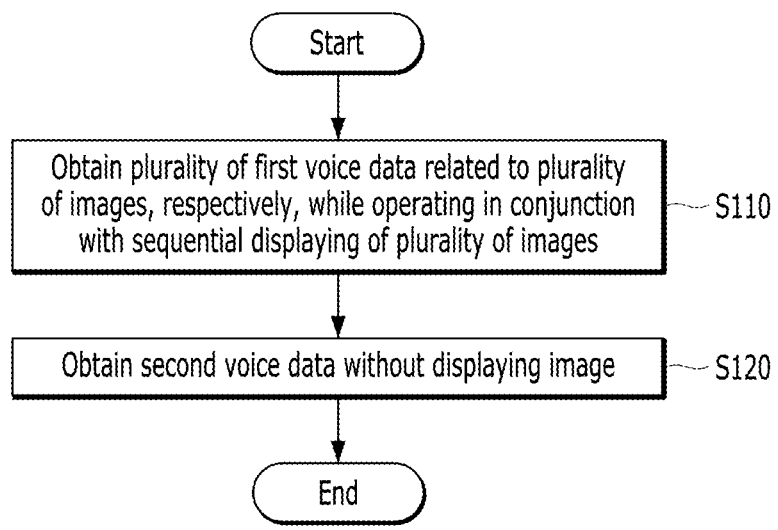
FIG. 2 is a flowchart for describing an example of a method of obtaining a plurality of first voice data and second voice data, that is, digital bio marker data for identifying dementia, according to some embodiments of the present disclosure.
Figure 3:
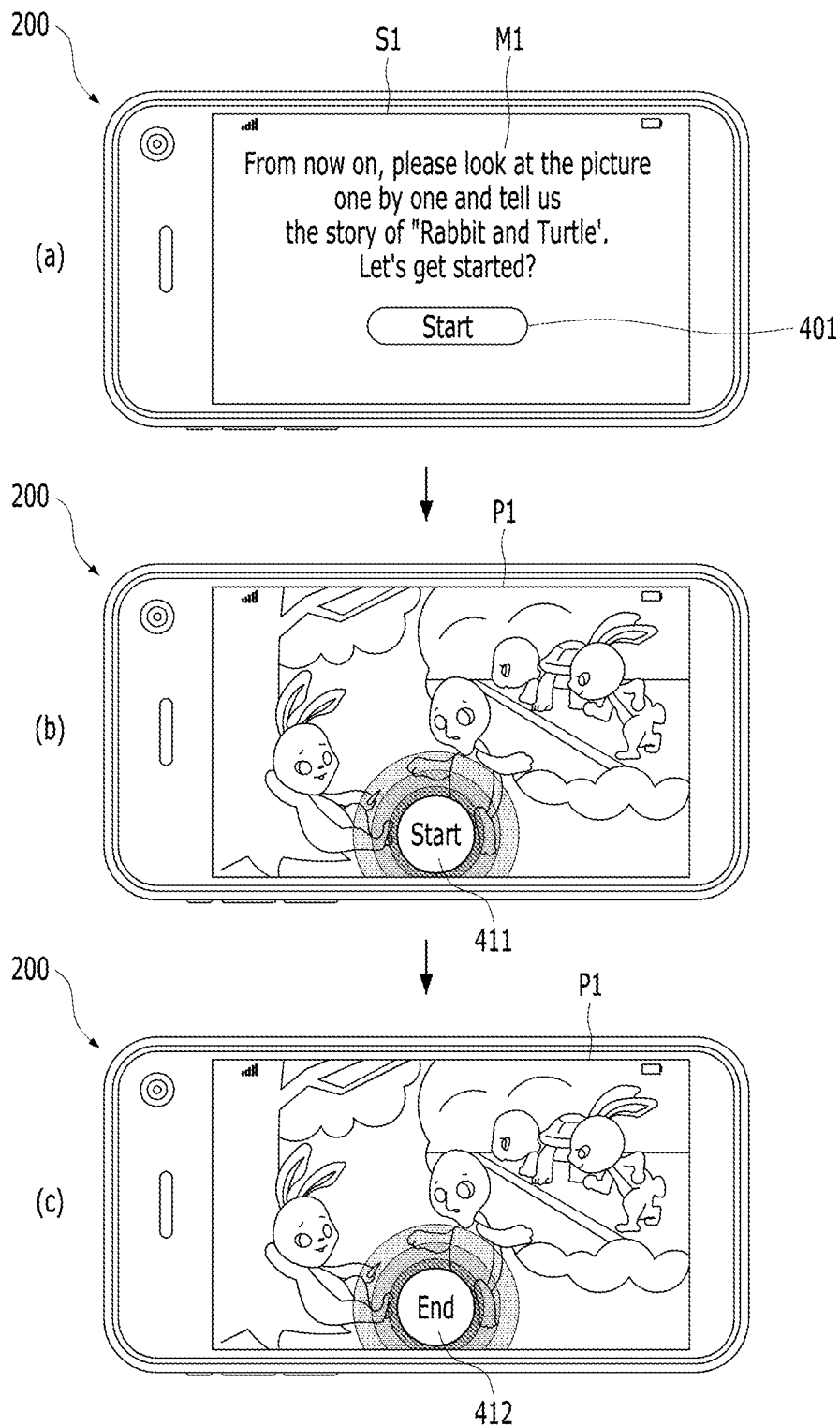
FIG. 3 is a diagram for describing an example of a method of obtaining a plurality of first voice data according to some embodiments of the present disclosure.
Figure 4:
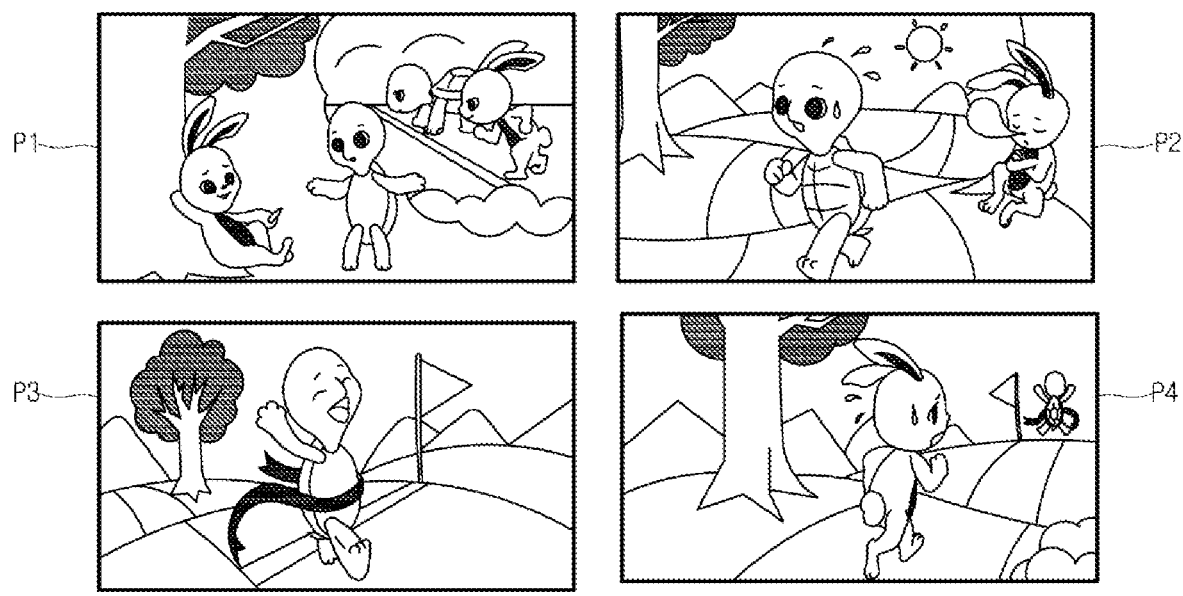
Figure 6:
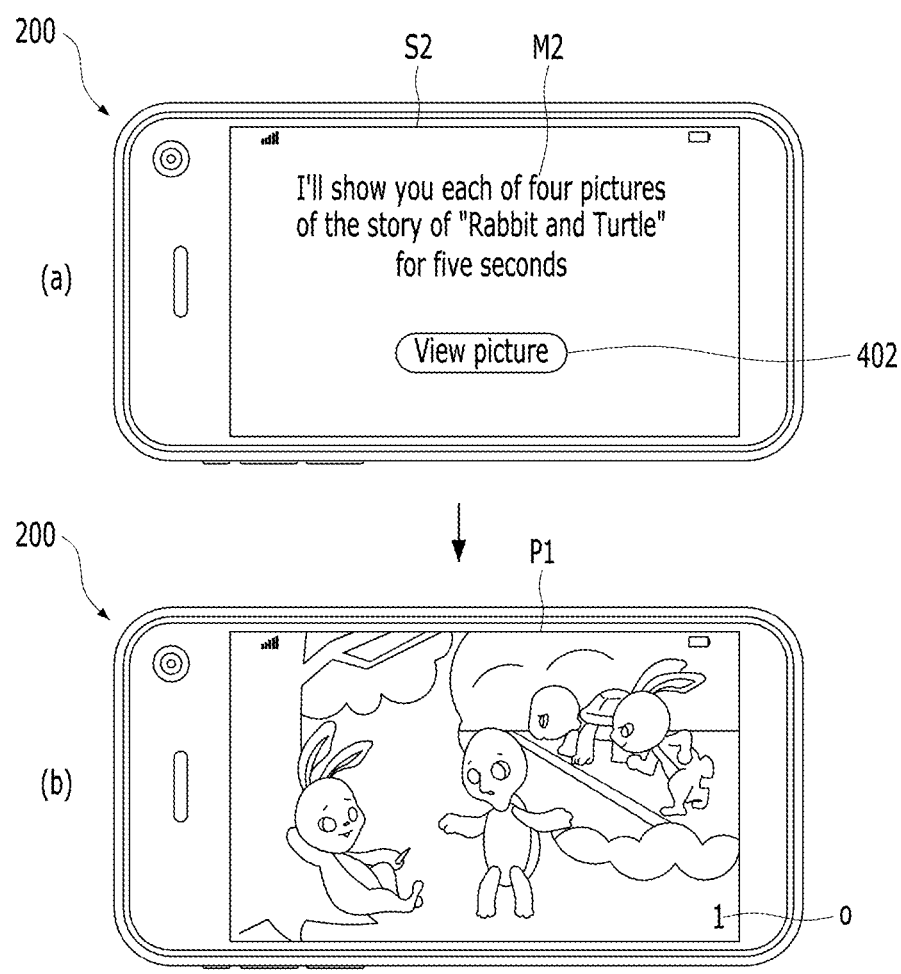
FIG. 6 is a diagram for describing an example of a task that is performed before a plurality of first voice data is obtained according to some embodiments of the present disclosure.
Figure 7:
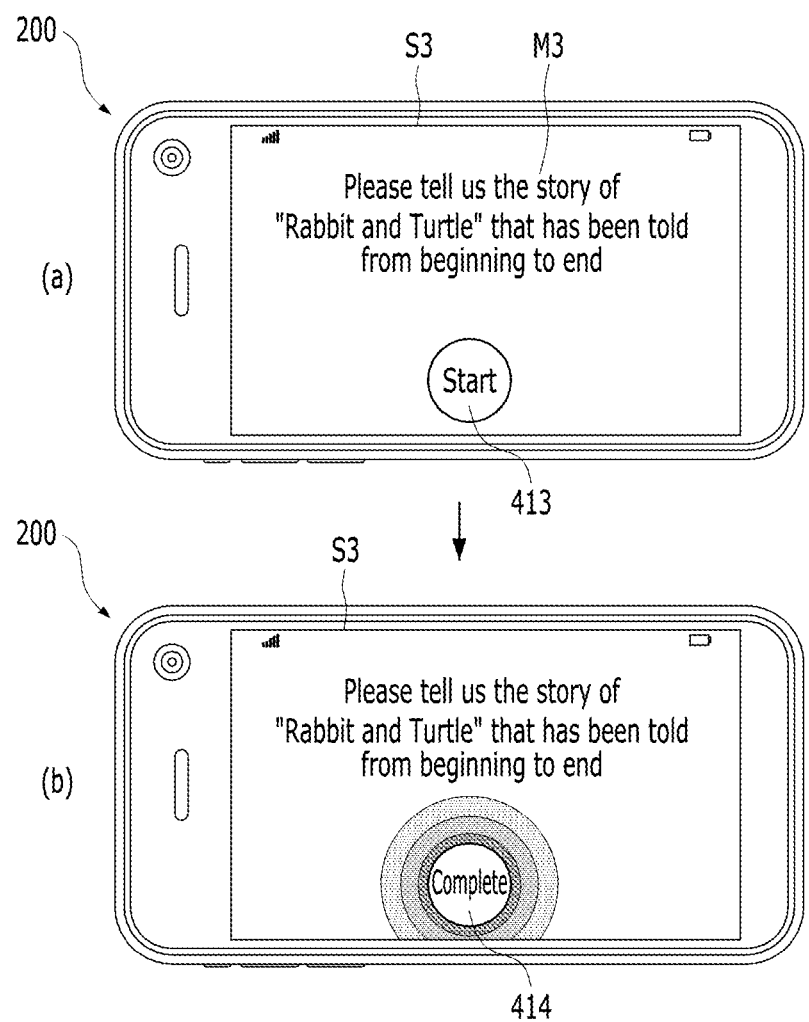
FIG. 7 is a diagram for describing an example of a method of obtaining second voice data according to some embodiments of the present disclosure.

FIG. 2 is a flowchart for describing an example of a method of obtaining a plurality of first voice data and second voice data, that is, digital bio marker data for identifying dementia, according to some embodiments of the present disclosure. FIG. 3 is a diagram for describing an example of a method of obtaining a plurality of first voice data according to some embodiments of the present disclosure. FIGS. 4 and 5 are diagrams for describing a plurality of images that is displayed when a plurality of first voice data is obtained according to some embodiments of the present disclosure. FIG. 6 is a diagram for describing an example of a task that is performed before a plurality of first voice data is obtained according to some embodiments of the present disclosure. FIG. 7 is a diagram for describing an example of a method of obtaining second voice data according to some embodiments of the present disclosure. In relation to FIGS. 2 to 7, contents that are redundant with the contents described in relation to FIG. 1 are not described again, and differences between them are described below.

Referring to FIG. 2, the processor 210 of the user terminal 200 may perform a first task for obtaining a plurality of first voice data related to a plurality of images, respectively, while operating in conjunction with the sequential displaying of the plurality of images (S110). In this case, the plurality of first voice data may include voice data that is obtained from timing at which a first touch input is input to timing at which a second touch input is input when an N (N is a natural number equal to or greater than 1)-th image, among the plurality of images, is displayed.

The first touch input may be a touch input to a first button (e.g., the start button) that is displayed along with the N-th image.

The second touch input may be a touch input to a second button in the state in which the second button has been displayed along with the N-th image instead of the first button in response to the first touch input.

A process of obtaining the plurality of first voice data is more specifically described with reference to FIG. 3.

Referring to (a) in FIG. 3, before obtaining a plurality of first voice data, that is, some of digital bio marker data for identifying dementia, the processor 210 of the user terminal 200 may control the display unit 250 so that the display unit 250 displays a description screen S1 that describes a task that needs to be performed by a user. In this case, the description screen S1 may include a message M1 that describes the task that needs to be performed by the user and a start button 401 that enables the first task for obtaining the plurality of first voice data to be started.

According to some embodiments of the present disclosure, a sound related to the message M1 (e.g., a voice that describes contents included in the message M1) may be output through the sound output unit 260, while operating in conjunction with the displaying of the message M1. If a user is made cognitive of a task that needs to be performed by the user through the output of the sound along with the message M1 as described above, the user can clearly understand the task that is now being performed by the user. Accordingly, there may be a poor possibility that a user may perform an erroneous task due to simple mistakes.

Referring to (b) in FIG. 3, the processor 210 of the user terminal 200 may control the display unit 250 so that the display unit 250 displays a primary image P1, among a plurality of images, based on a touch input to select the start button 401.

Specifically, the processor 210 of the user terminal 200 may control the display unit 250 so that the display unit 250 also displays a first button 411, when the primary image P1, among the plurality of images, is displayed. In this case, the plurality of images is images related to one story, and may be images that are displayed in a display order. The primary image P1 may be the first image that is displayed for the first time.

A method of displaying images if the plurality of images has been stored in the storage 120 of the device 100 and a method of displaying images if the plurality of images has been stored in the storage 220 of the user terminal 200 may be different from each other.

For example, if the plurality of images has been stored in the storage 120 of the device 100, the processor 210 of the user terminal 200 may control the communication unit 230 so that the communication unit 230 receives the primary image P1 after transmitting a primary image request signal to the device 100, when a touch input to select the start button 401 is detected. When receiving the primary image P1, the processor 210 of the user terminal 200 may control the display unit 250 so that the display unit 250 displays the primary image P1.

As another example, if the plurality of images has been stored in the storage 220 of the user terminal 200, the processor 210 may control the display unit 250 so that the display unit 250 displays the primary image P1, among the plurality of images that has been stored in the storage 220, when a touch input to select the start button 401 is detected.

Referring to (c) in FIG. 3, when a first touch input to the first button 411 is input, the processor 210 may start to obtain first voice data related to the primary image P1 by activating the sound acquisition unit 240, while operating in conjunction with the displaying of the second button 412 along with the primary image P1 instead of the first button.

When a touch input to the first button 411 is detected, a second button 412 may be displayed instead of the first button 411 while a preset effect is added to the second button 412. For example, an effect having a form in which a preset color is spread centering around the second button 412 may be added to the second button 412. However, the preset effect is not limited to the aforementioned example, and various effects may be added to the second button 412. When the preset effect is added to the second button 412 as described above, a user can cognize that the first voice data is now being obtained.

When a second touch input to the second button 412 is input, the processor 210 may terminate the acquisition of the first voice data and deactivate the sound acquisition unit 240. That is, the first voice data that is obtained when the primary image is displayed may be recorded voice data of a voice of a user from timing at which the first touch input is input to timing at which the second touch input is input. Furthermore, the first voice data that is obtained when the primary image is displayed may be recorded as the first voice data related to the primary image.

According to some embodiments of the present disclosure, when the second touch input to the second button 412 is input, the processor 210 may control the display unit 250 so that the display unit 250 displays a secondary image (P2 in FIG. 4) instead of the primary image P1. That is, an N-th image (N is a natural number equal to or greater than 1) may be changed into an (N+1)-th image in response to the second touch input.

When the secondary image is displayed, the processor 210 may identically perform the aforementioned task in relation to (b) in FIG. 3 and (c) in FIG. 3. That is, when a touch input of a user for the second button 412 is detected as described above, the processor 210 may sequentially change an image into a next image, and may additionally obtain first voice data related to the next image. In this way, the processor 210 may obtain a plurality of first voice data related to all images that are related to a selected story.

According to some embodiments of the present disclosure, a plurality of images is images related to one story. The plurality of images may also be changed when a story title is different.

A plurality of images related to a plurality of stories, respectively, may be stored in the storage 120 of the device 100 or the storage 220 of the user terminal 200.

Referring to FIG. 5, a plurality of stories may have different story titles. In this case, the stories may be stories, such as Aesop's Fables and a children's story each having one plot.

For example, a plurality of stories may include at least a first story, a second story, a third story, and a fourth story. In this case, a story title of the first story may be Rabbit and Turtle, a story title of the second story may be Kongjwi Patjwi, a story title of the third story may be Sun and Moon, and a story title of the fourth story may be Heungbu and Nolbu, but the present disclosure is not limited thereto.

The number of images related to each of a plurality of stories may be the same or different.

For example, the number of images related to each of the first story, the second story, and the third story may be four. The number of images related to the fourth story may be five, but the present disclosure is not limited thereto.

In the present disclosure, a plurality of images that is displayed in the user terminal 200 may be images related to any one story, among the plurality of aforementioned stories.

Any one of the plurality of stories may be randomly selected, and may be selected in a preset order, but the present disclosure is not limited thereto.

Referring to FIG. 4, a plurality of images P1, P2, P3, and P4 related to one story may be different from each other, and may be stored in the storage 120 of the device 100 or the storage 220 of the user terminal 200, but the present disclosure is not limited thereto.

Furthermore, the order of each of the plurality of images P1, P2, P3, and P4 may have been determined. Accordingly, when the plurality of images P1, P2, P3, and P4 is displayed in the user terminal 200, the plurality of images P1, P2, P3, and P4 may be sequentially displayed.

Specifically, when a second touch input to the second button 412 that is displayed when the primary image P1 is displayed is detected, the secondary image P2 may be displayed on the display unit 250 of the user terminal 200. When a second touch input to the second button 412 that is displayed when the secondary image P2 is displayed is detected, the tertiary image P3 may be displayed on the display unit 250 of the user terminal 200. In this way, all of the plurality of images P1, P2, P3, and P4 may be displayed on the display unit 250 of the user terminal 200.

According to some embodiments of the present disclosure, prior to the first task for obtaining the plurality of first voice data related to the plurality of images while operating in conjunction with the sequential displaying of the plurality of images, a task for sequentially displaying each of the plurality of images for a preset time may be performed without obtaining voice data. This is described in detail with reference to FIG. 6.

Referring to (a) in FIG. 6, prior to a task for sequentially displaying each of a plurality of images for a preset time, the processor 210 may control the display unit 250 so that the display unit 250 displays a description screen S2 that describes a task that needs to be performed by a user. In this case, the description screen S2 may include a message M2 that describes a task that needs to be performed by the user and a start button 402 that enables the task for sequentially displaying each of the plurality of images for a preset time to be started.

According to some embodiments of the present disclosure, a sound related to the message M2 (e.g., a voice that describes contents included in the message M2) may be output through the sound output unit 260, while operating in conjunction with the displaying of the message M2. If a user is made cognitive of a task that needs to be performed by the user through the output of the sound along with the message M2 as described above, the user can clearly understand the task that is now being performed by the user. Accordingly, the user's concentration can be improved.

Referring to (b) in FIG. 6, the processor 210 of the user terminal 200 may control the display unit 250 so that the display unit 250 first displays the primary image P1, among the plurality of images, based on a touch input to select the start button 402.

Specifically, the processor 210 of the user terminal 200 may control the display unit 250 so that the display unit 250 also displays information O related to the order of the primary image P1 when the primary image P1, among a plurality of images, is displayed. In this case, the plurality of images is images related to one story, and may be images that are displayed in their display orders. The primary image P1 may be the first image that is displayed for the first time.

The information O related to the order of an image may include a number. That is, since the primary image P1 is the first image, a number 1 may be included in the information O related to the order of the primary image P1, but the present disclosure is not limited thereto.

According to some embodiments of the present disclosure, the primary image may be changed into a secondary image after being displayed for a preset time (e.g., five seconds), but the present disclosure is not limited thereto.

When an image that is displayed on the display unit 250 of the user terminal 200 is changed into the secondary image, the information O related to the order of the image may also be changed.

For example, since the secondary image is the second image, a number 2 may be included in the information O related to the order of the secondary image, but the present disclosure is not limited thereto.

That is, an image that is displayed on the display unit 250 of the user terminal 200 may be sequentially changed. When the image is changed, the information O related to the order of the image may also be changed.

Referring back to FIG. 2, the processor 210 of the user terminal 200 may perform a second task for obtaining second voice data without displaying an image (S120).

The second voice data may be voice data that is obtained from timing at which a third touch input is input to timing at which a fourth touch input is input on a screen that is displayed when a second task is performed, but the present disclosure is not limited thereto. In this case, the third touch input may be a touch input to a third button (e.g., the start button) that is displayed when the second task is performed. Furthermore, the fourth touch input may be a touch input to a fourth button in the state in which the fourth button has been displayed instead of the third button, in response to the third touch input.

Specifically, referring to (a) in FIG. 7, before the second task is performed, the processor 210 may control the display unit 250 so that the display unit 250 displays a description screen S3 that describes a task that needs to be performed by a user. In this case, the description screen S3 may include a message M3 that describes a task that needs to be performed by a user and a start button 413 related to the acquisition of the second voice data. In this case, the message M3 may include contents indicating that a story related to a plurality of images displayed in the first task needs to be spoken.

According to some embodiments of the present disclosure, a sound related to the message M3 (e.g., a voice that describes contents included in the message M3) may be output through the sound output unit 260 while operating in conjunction with the displaying of the message M3. If a user is made cognitive of a task that needs to be performed by the user through the output of the sound along with the message M3 as described above, the user can clearly understand the task that is now being performed by the user. Accordingly, the user's concentration can be improved.

Referring to (b) in FIG. 7, when a touch input to select the third button 413 is input, the processor 210 of the user terminal 200 may control the display unit 250 so that the display unit 250 displays a fourth button 414 on the screen S3 instead of the third button 413. Furthermore, the processor 210 may start to obtain the second voice data by activating the sound acquisition unit 240 without displaying a separate image on the screen S3.

When a touch input to the third button 413 is detected, a preset effect may be displayed while the preset effect is added to the fourth button 414 that is displayed instead of the third button 413. For example, an effect having a form in which a preset color is spread around the fourth button 414 may be added to the fourth button 414. However, the preset effect is not limited to the aforementioned example, and various effects may be added to the fourth button 414. When the preset effect is added to the fourth button 414 as described above, a user can cognize that the second voice data is now being obtained.

When the fourth touch input to the fourth button 414 is input, the processor 210 may terminate the acquisition of the second voice data, and may deactivate the sound acquisition unit 240. That is, the second voice data may be recorded voice data of a voice of a user from timing at which the third touch input to select the third button 413 is input to timing at which the fourth touch input is input.

According to some embodiments of the present disclosure, the processor 210 of the user terminal 200 may control the communication unit 230 so that the communication unit 230 transmits the plurality of first voice data and the second voice data to the device 100.

For example, after obtaining all of the plurality of first voice data and the second voice data, the processor 210 may control the communication unit 230 so that the communication unit 230 transmits the plurality of first voice data and the second voice data to the device 100.

As another example, after obtaining all of the plurality of first voice data, the processor 210 may control the communication unit 230 so that the communication unit 230 transmits the plurality of first voice data to the device 100. Furthermore, after obtaining the second voice data, the processor 210 may control the communication unit 230 so that the communication unit 230 transmits the second voice data to the device 100. That is, before the second task is performed after all of the plurality of first voice data is obtained through the first task, the processor 210 may control the communication unit 230 so that the communication unit 230 first transmits the plurality of first voice data to the device 100 and then transmits the second voice data to the device 100.

As still another example, the processor 210 may control the communication unit 230 so that the communication unit 230 transmits the plurality of first voice data and the second voice data to the device 100 whenever the plurality of first voice data and the second voice data are obtained.

However, the aforementioned examples are merely examples of the present disclosure, and the present disclosure is not limited to the aforementioned examples.

After receiving all of the plurality of first voice data and the second voice data, the processor 110 of the device 100 may identify whether a user of the user terminal 200 has dementia. This is more specifically described with reference to FIG. 8.

Figure 8:
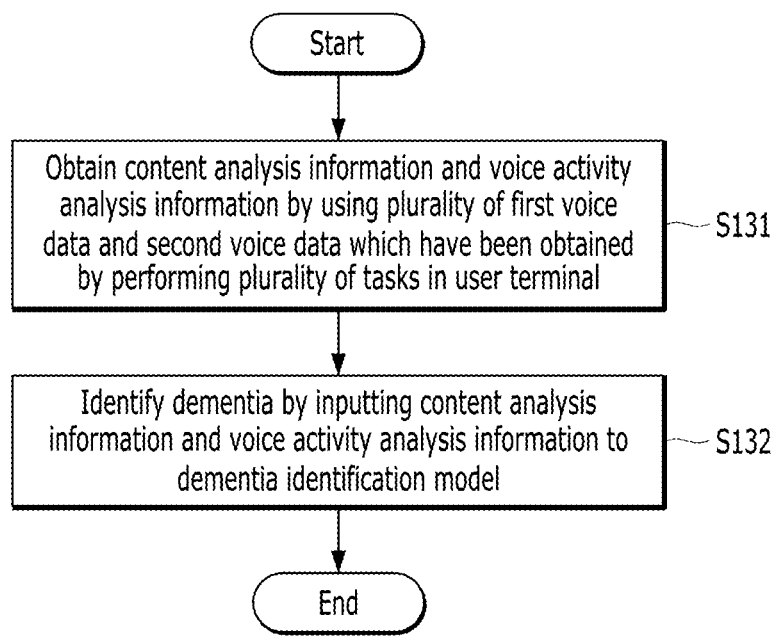
FIG. 8 is a flowchart for describing an example of a method of identifying dementia based on voice data according to some embodiments of the present disclosure.

FIG. 8 is a flowchart for describing an example of a method of identifying dementia based on voice data according to some embodiments of the present disclosure. FIG. 9 is a diagram for describing an example of keywords and analogues which are used when content analysis information is obtained according to some embodiments of the present disclosure. In relation to FIG. 8, contents that are redundant with the contents described in relation to FIGS. 1 to 7 are not described again, and differences between them are described below.

Referring to FIG. 8, the at least one processor 110 of the device 100 may obtain content analysis information and voice activity analysis information by using the plurality of first voice data and the second voice data which have been obtained by performing a plurality of tasks in the user terminal 200 (S131).

The content analysis information may mean information that is obtained by analyzing the contents of the plurality of first voice data and the second voice data. The voice activity analysis information may mean information indicative of a speech rate or response time of a user of the user terminal 200, but the present disclosure is not limited thereto.

In the present disclosure, the voice activity analysis information may include speech rate information and response time information of a user of the user terminal.

The speech rate information may be calculated based on the number of syllables included in each of the plurality of first voice data and the second voice data and a total time for which a voice of the user is present in each of the plurality of first voice data and the second voice data.

For example, the processor 110 may calculate a speech rate by dividing a total time for which the voice of the user is present in each of the plurality of first voice data and the second voice data by the number of syllables included in each of the plurality of first voice data and the second voice data.

In the present disclosure, a method of calculating the speech rate information is not limited to the aforementioned example.

The response time information may mean information on the time that is delay until a user talks after pressing the start button, but the present disclosure is not limited thereto.

The response time information may include information that is calculated based on information on first timing at which a voice of a user is present in each of the plurality of first voice data and information that is calculated based on information on second timing at which a voice of the user is present in the second voice data.

For example, when a voice of a user appears for 3 second in the plurality of first voice data or the second voice data, timing for which the voice of the user is present may be 3 seconds.

However, in the present disclosure, the aforementioned example is merely an example, and the present disclosure is not limited to the aforementioned example.

The plurality of tasks may include a first task for obtaining the plurality of first voice data related to a plurality of images, respectively, while operating in conjunction with the sequential displaying of the plurality of images and a second task for obtaining the second voice data without displaying an image. This has been described with reference to FIGS. 1 to 7, and a detailed description thereof is omitted.

In the present disclosure, the processor 110 may convert the plurality of first voice data into a plurality of first text data, and may convert the second voice data into second text data. In this case, when the plurality of first voice data is converted into the plurality of first text data and the second voice data is converted into the second text data, an algorithm related to a voice recognition technology (e.g., speech to text (STT)) may be used, but the present disclosure is not limited thereto.

The algorithm related to a voice recognition technology (e.g., STT) for converting voice data into text data may be stored in the storage 120 of the device 100. For example, the algorithm related to the voice recognition technology may be a hidden Markov model (HMM).

The processor 110 may obtain the content analysis information by using the plurality of first text data and the second text data. In this case, the content analysis information may include first information on a ratio of an interjection to all syllables of the plurality of first text data and the second text data, second information indicative of a degree in which a keyword related to each of a plurality of images is included in the plurality of first text data and the second text data, and third information indicative of a degree in which an analogue of a keyword related to each of the plurality of images is included in the plurality of first text data and the second text data, but the present disclosure is not limited thereto.

According to a conventional technology, a case in which dementia is identified by using the interjection ratio is not present. However, if dementia is identified by using the interjection ratio as in the present disclosure, the accuracy of the identification of dementia can be further improved.

Referring to FIG. 9, a plurality of keywords 510 related to a plurality of images, respectively, and a plurality of analogues 520 related to each of the plurality of keywords may be stored in the storage 120 of the device 100 according to the present disclosure. In this case, since the plurality of images is different images, the plurality of keywords and the plurality of analogues related to each of the plurality of keywords may be different for each image.

In some embodiments of the present disclosure, the processor 110 may calculate a degree in which a keyword related to a primary image and a plurality of analogues (e.g., a ratio of keywords and a ratio of analogues to all words that are included in text data), among a plurality of images, are included in the text data converted from voice data that is obtained when the primary image is displayed. Furthermore, the processor 110 may calculate a degree in which a keyword related to a secondary image, among a plurality of images, and a plurality of analogues are included in text data converted from voice data that is obtained when the secondary image is displayed. In this way, the processor 110 may calculate a degree in which keywords and a plurality of analogues are included in all of the plurality of first voice data.

According to some embodiments of the present disclosure, the processor 110 may calculate a degree in which a plurality of keywords related to all of a plurality of images and a plurality of analogues related to each of the plurality of keywords are included in second text data converted from the second voice data.

The plurality of keywords and the plurality of analogues related to each of the plurality of keywords may be mutually mapped and may be stored in the storage 120 in a table form as in FIG. 9, but the present disclosure is not limited thereto. A plurality of keywords and analogues related to the plurality of keywords may be stored in the storage 120 in various forms.

Referring back to FIG. 8, the processor 110 may identify whether a user of the user terminal 200 has dementia by inputting, to a dementia identification model, the content analysis information and the voice activity analysis information that have been obtained by using the plurality of first voice data and the second voice data (S132).

Specifically, the processor 110 may calculate a score value by inputting the content analysis information and the voice activity analysis information to the dementia identification model. Furthermore, the processor 110 may identify dementia based on the score value.

For example, the processor 110 may determine whether a user of the user terminal 200 has dementia based on whether the score value is greater than a preset threshold. That is, when recognizing that the score value output by the dementia identification model is greater than the preset threshold, the processor 110 may determine that the user has dementia. When recognizing that the score value output by the dementia identification model is equal to or smaller than the preset threshold, the processor 110 may determine that the user does not have dementia.

The aforementioned example is merely an example, and the present disclosure is not limited to the aforementioned examples.

In the present disclosure, the dementia identification model may be a deep learning model whose learning has been completed by using digital bio marker data of test users, which has been obtained through the method described in the present disclosure, but the present disclosure is not limited thereto.

In the present disclosure, since dementia is identified based on the content analysis information and the voice activity analysis information that are obtained by using the plurality of first voice data and the second voice data, the plurality of first voice data and the second voice data may be considered as digital bio marker data for identifying dementia.

120 people in a normal cognitive group and 9 people in a cognitively impaired group conducted experiments in order to identify whether they had dementia by using their user terminals. The goal of this experiment was to confirm the accuracy of the pre-learned dementia identification model It was confirmed that classification accuracy calculated through the aforementioned experiments was 80% or more.

According to at least one of the aforementioned several embodiments of the present disclosure, dementia may be accurately diagnosed in a way that a patient rarely feels rejection.

In an embodiment of the present disclosure, the configurations and methods of the aforementioned several embodiments of the device 100 are not limitedly applied, and all or parts of each of the embodiments may be selectively combined to allow various modifications.

Various embodiments described in the present disclosure may be implemented in a computer or similar device-readable recording medium using, for example, software, hardware, or a combination thereof.

According to hardware implementation, some embodiments described herein may be implemented using at least one of application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, and other electrical units for performing functions. In some cases, some embodiments described in the present disclosure may be implemented with at least one processor.

According to software implementation, some embodiments such as the procedures and functions described in the present disclosure may be implemented as separate software modules. Each of the software modules may perform one or more functions, tasks, and operations described in the present disclosure. A software code may be implemented as a software application written in a suitable programming language. In this case, the software code may be stored in the storage 120 and executed by at least one processor 110. That is, at least one program command may be stored in the storage 120, and the at least one program command may be executed by the at least one processor 110.

The method of identifying dementia by the at least one processor 110 of the device 100 using the dementia identification model according to some embodiments of the present disclosure may be implemented as code readable by the at least one processor in a recording medium readable by the at least one processor 110 provided in the device 100. The at least one processor-readable recording medium includes all types of recording devices in which data readable by the at least one processor 110 is stored. Examples of the at least one processor-readable recording medium includes read only memory (ROM), random access memory (RAM), CD-ROM, a magnetic tape, a floppy disk, and an optical data storage device.

Meanwhile, the method in which the processor 210 of the user terminal 200 acquires voice data, which is digital biomarker data for identifying dementia can be implemented as a code readable by at least one processor in a recording medium readable by the processor 210 provided in the user terminal 200. The at least one processor-readable recording medium includes all types of recording devices in which data readable by the at least one processor 110 is stored. Examples of the at least one processor-readable recording medium includes read only memory (ROM), random access memory (RAM), CD-ROM, a magnetic tape, a floppy disk, and an optical data storage device.

Although the present disclosure has been described with reference to the accompanying drawings, this is only an embodiment and the present disclosure is not limited to a specific embodiment. Various contents that can be modified by those of ordinary skill in the art to which the present disclosure belongs also belong to the scope of rights according to the claims. In addition, such modifications should not be understood separately from the technical spirit of the present disclosure.

What is claimed is:

1. A method of identifying, by at least one processor of a device, dementia, the method comprising:
    obtaining content analysis information and voice activity analysis information by using a plurality of first voice data and a second voice data which have been obtained by performing a plurality of tasks in a user terminal; and
    identifying dementia by inputting the content analysis information and the voice activity analysis information to a dementia identification model,
    wherein the content analysis information comprises information on a first ratio of at least one keyword stored in storage to all words spoken by a user, which have been generated by analyzing the plurality of first voice data and the second voice data, and information on a second ratio of at least one analogue related to the at least one keyword to all the words, wherein the information on the first ratio comprises:

information on a ratio of an N-th keyword related to an N-th image displayed in the user terminal when N-th voice data, among the plurality of first voice data, is obtained to all words spoken by the user, which have been generated by analyzing the N-th voice data;

information on a ratio of an (N+1)-th keyword related to an (N+1)-th image displayed in the user terminal when (N+1)-th voice data, among the plurality of first voice data, is obtained to all words spoken by the user, which has been generated by analyzing the (N+1)-th voice data; and information on a ratio of a plurality of keywords related to a plurality of images comprising the N-th image and the (N+1)-th image displayed in the user terminal when the plurality of first voice data is obtained to all words spoken by the user, which have been generated by analyzing the second voice data, wherein the information on the second ratio comprises:

information on a ratio of an N-th analogue mapped to the N-th keyword related to the N-th image displayed in the user terminal when the N-th voice data, among the plurality of first voice data, is obtained to all the words spoken by the user, which have been generated by analyzing the N-th voice data;

information on a ratio of an (N+1)-th analogue mapped to the (N+1)-th keyword related to the (N+1)-th image displayed in the user terminal when the (N+1)-th voice data, among the plurality of first voice data, is obtained to all the words spoken by the user, which have been generated by analyzing the (N+1)-th voice data; and information on a ratio of a plurality of analogues mapped to the plurality of keywords related to the plurality of images comprising the N-th image and the (N+1)-th image displayed in the user terminal when the plurality of first voice data is obtained to all the words spoken by the user, which have been generated by analyzing the second voice data, wherein the (N+1)-th image is an image changed in response to a touch input when the N-th image is displayed, and wherein the N is a natural number equal to or greater than 1.

2. The method of claim 1, wherein the obtaining of the content analysis information and the voice activity analysis information by using the plurality of first voice data and the second voice data which have been obtained by performing the plurality of tasks in the user terminal comprises:

changing the plurality of first voice data into a plurality of first text data;

converting the second voice data into second text data; and obtaining the content analysis information by using the plurality of first text data and the second text data.

3. The method of claim 2, wherein the content analysis information comprises first information on a ratio of an interjection to all syllables of the plurality of first text data and the second text data.

4. The method of claim 3, wherein:

the information on the first ratio is generated by analyzing a degree in which the at least one keyword is included in each of the plurality of first text data and the second text data, and the information on the second ratio is generated by analyzing a degree in which the at least one analogue is included in each of the plurality of first text data and the second text data.

5. The method of claim 1, wherein the voice activity analysis information comprises speech rate information of a user of the user terminal and response time information of the user.

6. The method of claim 5, wherein the response time information comprises:

information calculated based on information on first timing at which a voice of the user is present in each of the plurality of first voice data; and information calculated based on information on second timing at which a voice of the user is present in the second voice data.

7. The method of claim 1, wherein the plurality of tasks comprises:

a first task for obtaining the plurality of first voice data related to the plurality of images, respectively, while operating in conjunction with a sequential displaying of the plurality of images related to one story one by one; and a second task for obtaining the second voice data while displaying information on the one story without displaying an image.

8. The method of claim 7, wherein the plurality of first voice data comprises:

the N-th voice data that is obtained from timing at which a touch input to a start button is input to timing at which a touch input to an end button is input when the N-th image, among the plurality of images, is displayed; and the (N+1)-th voice data that is obtained from timing at which a touch input to a start button is input to timing at which a touch input to an end button is input when the (N+1)-th image, among the plurality of images, is displayed.

9. The method of claim 7, wherein the second voice data is voice data that is obtained from timing at which a third touch input is input to timing at which a fourth touch input is input on a screen that is displayed when the second task is performed.

10. The method of claim 9, wherein:

the third touch input is a touch input to a third button that is displayed when the second task is performed, and the fourth touch input is a touch input to a fourth button in a state in which the fourth button has been displayed instead of the third button, in response to the third touch input.

11. A computer program stored in a computer-readable storage medium, wherein when the computer program is executed by at least one processor of a device, the computer program performs steps of identifying dementia, wherein the steps comprises:

obtaining content analysis information and voice activity analysis information by using a plurality of first voice data and second voice data which have been obtained by performing a plurality of tasks; and identifying dementia by inputting the content analysis information and the voice activity analysis information to a dementia identification model, wherein the content analysis information comprises information on a first ratio of at least one keyword stored in storage to all words spoken by a user, which have been generated by analyzing the plurality of first voice data and the second voice data, and information on a second ratio of at least one analogue related to the at least one keyword to all the words, wherein the information on the first ratio comprises:

information on a ratio of an N-th keyword related to an N-th image displayed in the user terminal when N-th voice data, among the plurality of first voice data, is obtained to all words spoken by the user, which have been generated by analyzing the N-th voice data;

information on a ratio of an (N+1)-th keyword related to an (N+1)-th image displayed in the user terminal when (N+1)-th voice data, among the plurality of first voice data, is obtained to all words spoken by the user, which has been generated by analyzing the (N+1)-th voice data; and information on a ratio of a plurality of keywords related to a plurality of images comprising the N-th image and the (N+1)-th image displayed in the user terminal when the plurality of first voice data is obtained to all words spoken by the user, which have been generated by analyzing the second voice data, wherein the information on the second ratio comprises:

information on a ratio of an N-th analogue mapped to the N-th keyword related to the N-th image displayed in the user terminal when the N-th voice data, among the plurality of first voice data, is obtained to all the words spoken by the user, which have been generated by analyzing the N-th voice data;

information on a ratio of an (N+1)-th analogue mapped to the (N+1)-th keyword related to the (N+1)-th image displayed in the user terminal when the (N+1)-th voice data, among the plurality of first voice data, is obtained to all the words spoken by the user, which have been generated by analyzing the (N+1)-th voice data; and information on a ratio of a plurality of analogues mapped to the plurality of keywords related to the plurality of images comprising the N-th image and the (N+1)-th image displayed in the user terminal when the plurality of first voice data is obtained to all the words spoken by the user, which have been generated by analyzing the second voice data, wherein the (N+1)-th image is an image changed in response to a touch input when the N-th image is displayed, and wherein the N is a natural number equal to or greater than 1.

12. A device for identifying dementia, the device comprising:

storage in which at least one program instruction has been stored; and at least one processor configured to perform the at least one program instruction, wherein the at least one processor is configured to:

obtain content analysis information and voice activity analysis information by using a plurality of first voice data and second voice data which have been obtained by performing a plurality of tasks; and identify dementia by inputting the content analysis information and the voice activity analysis information to a dementia identification model, wherein the content analysis information comprises information on a first ratio of at least one keyword stored in storage to all words spoken by a user, which have been generated by analyzing the plurality of first voice data and the second voice data, and information on a second ratio of at least one analogue related to the at least one keyword to all the words, wherein the information on the first ratio comprises:

information on a ratio of an N-th keyword related to an N-th image displayed in the user terminal when N-th voice data, among the plurality of first voice data, is obtained to all words spoken by the user, which have been generated by analyzing the N-th voice data;

information on a ratio of an (N+1)-th keyword related to an (N+1)-th image displayed in the user terminal when (N+1)-th voice data, among the plurality of first voice data, is obtained to all words spoken by the user, which has been generated by analyzing the (N+1)-th voice data; and information on a ratio of a plurality of keywords related to a plurality of images comprising the N-th image and the (N+1)-th image displayed in the user terminal when the plurality of first voice data is obtained to all words spoken by the user, which have been generated by analyzing the second voice data, wherein the information on the second ratio comprises:

information on a ratio of an N-th analogue mapped to the N-th keyword related to the N-th image displayed in the user terminal when the N-th voice data, among the plurality of first voice data, is obtained to all the words spoken by the user, which have been generated by analyzing the N-th voice data;

information on a ratio of an (N+1)-th analogue mapped to the (N+1)-th keyword related to the (N+1)-th image displayed in the user terminal when the (N+1)-th voice data, among the plurality of first voice data, is obtained to all the words spoken by the user, which have been generated by analyzing the (N+1)-th voice data; and information on a ratio of a plurality of analogues mapped to the plurality of keywords related to the plurality of images comprising the N-th image and the (N+1)-th image displayed in the user terminal when the plurality of first voice data is obtained to all the words spoken by the user, which have been generated by analyzing the second voice data, wherein the (N+1)-th image is an image changed in response to a touch input when the N-th image is displayed, and wherein the N is a natural number equal to or greater than 1.

* * * * *